United States Patent [19]

Adrian et al.

[11] 4,057,724

[45] Nov. 8, 1977

[54] DETERMINATION OF THE ALCOHOL CONTENT OF BLOOD

[76] Inventors: Werner Karl Adrian, Im Roth 19, Ettlingen, Germany; Robert Frank Borkenstein, 821 S. High St., Bloomington, Ind. 47401

[21] Appl. No.: 667,847

[22] Filed: Mar. 17, 1976

[30] Foreign Application Priority Data

Mar. 17, 1975 Germany .............................. 2511771

[51] Int. Cl.² .............................................. G01N 21/26
[52] U.S. Cl. .................................... 250/343; 250/344
[58] Field of Search ........................ 250/342, 343, 344

[56] References Cited

U.S. PATENT DOCUMENTS

| | | | |
|---|---|---|---|
| 3,569,696 | 3/1971 | Karlson | 250/344 X |
| 3,792,272 | 2/1974 | Harte et al. | 250/343 |
| 3,969,626 | 7/1976 | Saltzman | 250/344 |

*Primary Examiner*—Archie R. Borchelt

*Attorney, Agent, or Firm*—Woodard, Weikart, Emhardt & Naughton

[57] ABSTRACT

A relationship exists between the concentration of ethanol in human breath and blood. Ethanol absorbs infrared energy in the region of 3.46 mu. In this method the concentration of ethanol in breath is measured by collecting a sample in a chamber and passing through it a filtered, directional, and interrupted beam of infra-red energy at 3.46 mu. The path length is fixed. The exit energy falls on a tuned radiant energy detector. This beam is compared with a similar beam of radiant energy not capable of being absorbed by ethanol. The two signals are fed into a differential amplifier which activates a servo-system that moves a tapered radiant-energy absorbing medium in the path of one of the energy beams until a null condition is achieved. The distance the tapered medium must be moved to establish the null condition is measured by a potentiometer operably associated with it. The potentiometer provides a signal that can be displayed by an analog or digital device calibrated directly in units of blood or breath ethanol concentration.

5 Claims, 1 Drawing Figure

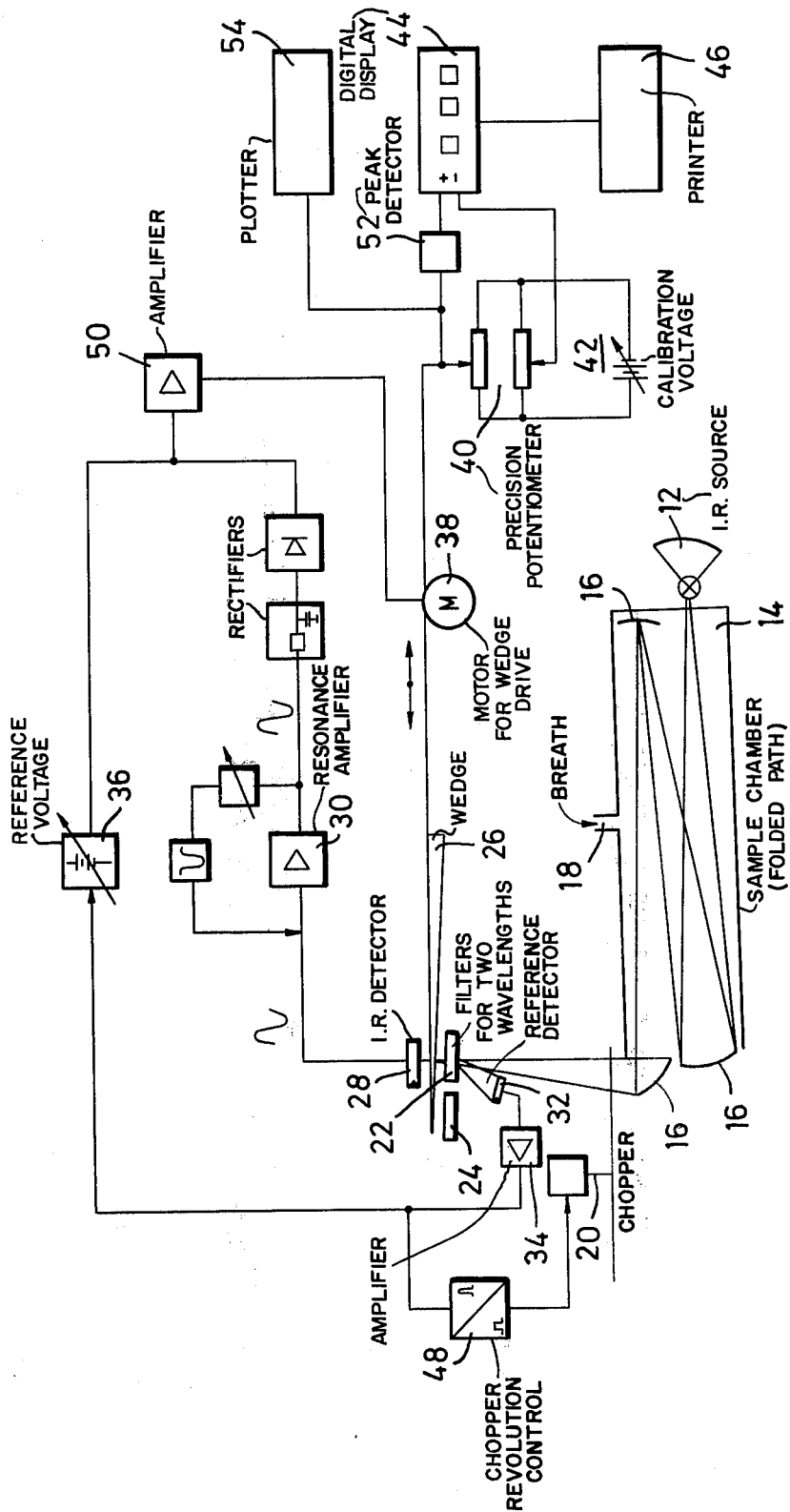

DETERMINATION OF THE ALCOHOL CONTENT OF BLOOD

The invention provides an apparatus for determining the alcohol content of blood by measuring the concentration of alcohol in exhaled breath. The apparatus includes a measuring chamber having an inlet via which exhaled breath can be blown in, a radiation inlet at one end of the measuring chamber and a radiation outlet at the other end of the measuring chamber. A radiation source in the form of a wide band thermal radiator is located upstream of the radiation inlet. An interrupting device is located in the path of the beam and a filter having a pass band at 3.46 $\mu$m is arranged as a tuned receiver downstream of the radiation outlet of the measuring chamber. A first photo-electric detector is arranged beyond the filter and a second detector is arranged in the path of the beam beyond the radiation outlet of the measuring chamber and in front of the filter. An amplifier is connected to the output of the first detector. A reference voltage source is connected to the output of the second detector, the outputs of the amplifier and the reference voltage source being connected to a differential amplifier. A drive motor is connected to the output of the differential amplifier. An absorption device is displaceable in and at right angles to the path of the beam between the radiation outlet of the measuring chamber and the photo-electric detector, the absorption device being in the form of a wedge connected to the drive motor and having absorption in the band width of the filter. The drive motor is arranged to automatically displace the wedge to maintain at zero the voltage at the output of the differential amplifier. An indicator is connected to the drive motor for the wedge and is arranged to indicate the position of the wedge in the path of the beam.

BACKGROUND OF THE INVENTION

1. Field of the Invention

The invention relates to arrangements for determining the alcohol content of blood.

2. Description of the Prior Art

Such an arrangement is already known in which the concentration of alcohol in exhaled breath is measured in a measuring chamber having an inlet through which exhaled breath can be blown in, a radiation inlet at one end of the measuring chamber and a radiation outlet at the other end of the measuring chamber, a radiation source upstream of the radiation inlet, an interrupting device in the path of a radiation beam, a tuned photoelectric receiving device downstream of the radiation outlet, an indicator connected to the receiving device, and an absorption device which is displaceable in and at right angles to the path of the beam between the radiation outlet of the measuring chamber and the photoelectric receiver.

An arrangement of this type for analysing gases is already known (see FIG. 3 of British patent specification No. 1,113,986) which includes two measuring chambers, a reference gas being introduced into one of the measuring chambers and the gas to be analysed being introduced into the other measuring chamber. A monochromatic light beam produced by a laser is transmitted through the two measuring chambers. Different absorption occurs in the two measuring chambers. These different absorptions lead to different intensities at the photo-electric receivers arranged at the radiation outlets. A differential voltage is formed from these differing intensities. The differential voltage is indicated and is indicative of, for example, the concentration of the gas to be analysed relative to the reference gas. Before entering the measuring chambers, the monochromatic light beam produced by the laser is modulated by means of a mechanically operating interrupting device. This facilitates amplification of the voltages produced by the receivers. Wedge-shaped displaceable attenuators are located in front of the receivers in the two radiation paths. Upon admitting the reference gas into one of the measuring chambers, the indication can be increased or decreased, set to zero or calibrated by displacing these attenuators. Thus, the absorption devices serve for adjustment and calibration. The prerequisites for accurate operation of, and accurate indication by, this arrangement are constant conditions, independent of temperature, in the two measuring chambers, uniform linear behaviour of the two receivers, constant or identically varying working points of the two amplifiers etc. Furthermore, the known arrangement requires a monochromatic laser acting as the source of radiation. A laser of this type is very expensive.

According to Henry's law, a relationship exists between the alcohol content of the blood and the alcohol content of the breath. A one part per thousand concentration of blood alcohol corresponds to 1 mg of ethyl alcohol per $cm^3$ of blood and leads to an alcohol content of 1 mg in 2100 $cm^3$ of exhaled alveolar breath. Thus, the blood alcohol concentration can be determined by measuring the quantity of alcohol contained in the exhaled air. The alcohol molecules contained in air absorb in the infrared range a6 3.46 $\mu$m. Thus, the quantity of alcohol in the breath and, correspondingly, the alcohol concentration in the blood can be determined by measuring the absorption at this wavelength. A known arrangement constructed in accordance with this principle includes a measuring chamber having an infrared radiator at one end and an infrared detector at its other end. A filter having a preferred band-pass width at 3.39 $\mu$m is located in front of the detector. The indicator connected to the detector is set to zero by the pure air admitted into the measuring chamber. The radiation passing through the measuring chamber is damped at the said wave length when breath containing alcohol is subsequently blown into the measuring chamber. The indication correspondingly drops and thus is indicative of the alcohol concentration in the breath or in the blood. Accurate and reproducible indication requires constant operation, a constant working point and extremely strict linearity of the detector and of the amplifier connected to the output thereof. Differences in the operating behavior between measuring the pure air and the alcohol-containing breath subsequently blown into measuring chamber are not admissible. However, these conditions can only be fulfilled with a high technical expenditure. A further complication is the fact that the properties of an infrared are greatly dependent upon the ambient temperature. Also, the source of infrared radiation must produce radiation which is constant with respect to intensity and composition both when measuring with pure air and when subsequently measuring the alcohol-containing breath.

A further basic difficulty in determining the alcohol concentration by means of the known arrangement is that the antilog of the signal produced by the detector has to be taken. This can be done with only a limited degree of accuracy by electronic means. The necessity of taking the antilog follows from the Lambert/Beer Law. This law describes the absorption in a gas and reads as follows:

$$\phi_e/\phi_o = e^{-mcd}$$

$\phi_o$ being the entering beam current and $\phi_e$ being the emerging beam current, $m$ being a material constant, $d$ being the length of the medium which is irradiated (length of path), and $c$ being the gas concentration in question.

Thus, the known arrangement (see U.S. Pat. No. 3,792,272) has only limited accuracy of measurement.

A device for comparing the intensity of two beams is also known. This device includes, inter alia, a variable attenuating member in the path of the beam. This attenuating member is displaced by means of a servo-motor until the difference between the intensity of the two beams has been reduced to zero. A recording device then records the adjusting travel of the attenuating member as a measured value for the equalized difference between the intensities (see German Auslegeschrift No. 1,084,490).

Based on this prior art, the basic object of the invention is to provide an arrangement for determining the blood alcohol content such that the blood alcohol content can be reproducibly determined with great accuracy despite a low expenditure on circuitry.

SUMMARY OF ILLUSTRATED EMBODIMENT OF THE INVENTION

In accordance with the invention, there is provided an arrangement for determing the alcohol content of blood by measuring the concentration of alcohol in exhaled breath, comprising a measuring chamber having an inlet via which exhaled breath can be blown in, a radiation inlet at one end of the measuring chamber and a radiation outlet at the other end of the measuring chamber, a radiation source in the form of a wide band thermal radiator located upstream of the radiation inlet, an interrupting device in the path of the beam, a filter having a pass band at 3.46 μm arranged as a tuned receiver downstream of the radiation outlet of the measuring chamber, a first photo-electric detector arranged beyond the filter, a second detector arranged in the path of the beam beyond the radiation outlet of the measuring chamber and in front of the filter, an amplifier connected to the output of the first detector, a reference voltage source connected to the output of the second detector, the outputs of the amplifier and the reference voltage source being connected to a differential amplifier, a drive motor connected to the output of the differential amplifier, an absorption device which is displaceable in and at right angles to the path of the beam between the radiation outlet of the measuring chamber and the photo-electric detector, the absorption device being in the form of a wedge connected to the drive motor and having absorption in the band width of the filter, the drive motor being arranged to automatically displace the wedge to maintain at zero the voltage at the output of the differential amplifier, and an indicator which is connected to the drive motor for the wedge and arranged to indicate the position of the wedge in the path of the beam.

The wide-band thermal radiator arranged at the inlet of the measuring chamber can be a simple incandescent lamp in a quartz bulb and is thus a very inexpensive source of radiation compared with a laser. The special advantage and the accuracy and constancy of measurement with the aforegoing arrangement result from the fact that the radiation is split up into two portions only beyond the outlet of the measuring chamber, one of which portions includes or supplies the measuring signal and the other portion acts as a control variable and a reference variable of the optical state of the measuring chamber. Operations are carried out simultaneously with both portions. Thus, errors do not occur which otherwise occur with the known arrangements by using two different measuring chambers or as a result of two successive measurements. The signal of the first detector is fed to a resonance amplifier or signal amplifier. The signal of the second detector is fed by way of an amplifier to a reference voltage source and controls the latter. The two voltages, that is the signal voltage and the reference voltage, are subtracted and the difference is amplified in the differential amplifier. The reference voltage source monitors, inter alia, the optical state of the measuring chamber and the radiation source. The voltage suplied by the reference voltage source changes upon a change in the intensity of radiation upon misting of mirrors provided in the measuring chamber for the purpose of reflecting and thus lengthening the radiation path. Thus, changes at the radiation outlet, not attributable to the alcohol content of the breath, are removed from the measurement in that equal voltages appearing in the measuring and control path are subtracted from one another.

In front of the first detector, which is struck by the infrared radiation with λ = 3.46 μm filtered out by the filter, there is arranged an absorption device made from quartz which absorbs a small amount of this radiation. The absorption device has a variable thickness $d$. Thus, its absorption is also variable. This absorption also obeys the Lambert/Beer Law. However, the exponents $m$ and $o$ are constant in this case. Only $d$ is variable. Thus, the varying of $d$ is proportional to $c$ in the path of the gas. The antilog of the equation can be taken in this manner and a linear relationship results between the thickness $d$ of the absorption device and the concentration $c$ to be measured. The absorption device is in the form of a wedge or two wedges which are displaceable relative to one another. The thickness $d$ of the absorption device is proportional to its displacement $s$ at right angles to the path of the beam. Thus, there also results a linear relationship between the distance $s$ and the concentration $c$ to be measured. Thus, the length $s$ of the path is directly indicative of the concentration. Alternatively, a single wedge may be used instead of two wedges which are displaceable relative to one another for the purpose of varying the thickness $d$. The diffraction of the beam then has to be taken into account.

Pure air is introduced into the measuring chamber in order to set up the apparatus. The absorption device is displaced such that a mean thickness of its material is irradiated and thus the radiation is pre-attenuated. The receiving device receiving the amplification of the wide-band unfiltered radiation is then set such that the signals in the two amplifiers are equal and the difference becomes zero. If the breath containing the alcohol is now introduced into the measuring chamber, the intensity of the infrared radiation filtered out of the entire range by the filter is reduced by absorption by the alcohol molecules, while the visible portion of the radiation reflected on the front face of the filter is not influenced by alcohol and does not cause any change in the reference voltage. This leads to a difference between the two voltages at the input of the differential amplifier whose output acts upon the drive motor of the wedge which acts as a servo-motor. This motor withdraws the wedge from the path of the beam and thus brings thinner portions of the wedge into the path of the beam. The absorption effected by the wedge is thus reduced. As soon as the absorption reduced by the withdrawal of the wedge is equal to the absorption effected by the alcohol molecules, the voltage difference at the differential amplifier again becomes zero and the displacement of the wedge is terminated. Thus, the measuring principle in accordance with the invention resides in counteracting the absorption occurring in the measuring chamber by opposing reduction of the absorption in the wedge. This has two advantages:

1. The displacement of the wedge, whose thickness can be ground to any optional degree of accuracy, is directly proportional to the concentration $c$. The displacement of the wedge can be converted into an electrical signal by means of a potentiometer which is located in, for example, an electrical bridge circuit, and the displacement of the wedge can be readily indicated. The indicated value can readily be given in parts per thousand of the blood alcohol content by varying the voltage across the bridge.
2. The filtered signal to be amplified in one of the amplifiers permanently has the same intensity, since the reduction in its intensity occurring in the measuring chamber is counteracted by attenuating the absorption in the wedge.

Thus, the amplifier always operates at the same operating point. The same applies to the detector. Thus, the measurement is rendered independent of the linearity characteristic of the amplifier and detector. The influences of temperature also have no effect. The ambient temperature has to remain constant only during the measuring operation.

In the case of diabetics and persons who have abstained from food for a long period of time, acetones can appear in the blood and, like alcohol, enter the alveoli of the lungs in the breath. However, acetone also has a $CH_3$ band, $\lambda_1 = 3.376$ and $\lambda_2$ at 3.482 $\mu m$. However, alcohol exhibits $CH_3$ and $CH_2$ bands, the later at $\lambda_1 = 2.417$ and $\lambda_2$ at 3.505 $\mu m$. Although the acetone concentrations are low, the result is falsified when using only one measuring wave length. Thus, in the case of alcoholized diabetics, there is no accurate indication as to which portion of the reading corresponds to the alcohol and which portion corresponds to the acetones in the breath. For this purpose, the filters are changed on a sliding device. The spectral centroids of the very narrow-band filters are chosen such that a difference between $CH_3$ and $CH_2$ absorption bands results. An acetone content in the breath can be deflected by this measure. This is effected by virtue of the fact that the filter provided for measuring the alcohol is exchangeable for a filter having a band width in the range of the greater absorption of acetone.

It has already been mentioned that the second detector is arranged in the path of the beam in front of the filter and thus receives the unfiltered radiation emerging directly from the measuring chamber. However, it must not be pushed into the path of the beam since it would otherwise mask the radiation. Preferably, the second detector is arranged in the range of reflection of the filter and receives the unfiltered radiation reflected from the front side of the filter.

The radiation is periodically interrupted by an interrupting device, such as a vane shutter, before entering or after emerging from the measuring chamber. By means of this known measure, one virtually obtains a carrier frequency which is modulated by the intensity fluctuations to be measured. The amplifiers can then be narrow-band amplifiers tuned to this carrier frequency, thus bringing the advantage of a higher signal-to-noise ratio. However, this carrier or operating frequency must be accurately complied with for satisfactory operation of the amplifiers. For this purpose, and in accordance with the invention, an arrangement for regulating the rotational speed of the interrupting device or of the vane shutter is additionally connected to the second detector and the frequency produced by the interrupting device and supplied by the detector as a control variable is compared with a desired value, and a regulating voltage dependent upon this comparison is fed to the drive motor of the interruptor.

DETAILED DESCRIPTION OF DRAWING

A block circuit diagram of one arrangement in accordance with the invention is shown in the drawing and will now be described, by way of example.

Radiation emanating from an IR radiation source 12 enters a measuring chamber 14. The path of the beam is reflected several times in the measuring chamber by mirrors 16, thus increasing the effective length of the beam. The reduction in intensity caused by the absorption correspondingly increases in accordance with the Lambert/Beer Law. The measuring signal is thus increased. Apertures 18 to enable breath to be blown in and to enable the breath to escape after measurement are located on the chamber 14. An interrupting device 20 is located at the outlet of the chamber 14, this device 20 comprising a motor having a rotary vane mounted on its shaft. Two IR filters 22,24, displaceable into the path of the beam, are located beyond the outlet of the measuring chamber. The band widths of the filters 22,24 are matched to the $CH_2$ or $CH_3$ valence bands. A wedge 26, absorbant in the range of radiation used, is located beyond the IR filter, and an IR detector 28 is arranged beyond the wedge 26. A resonance amplifier 30 is connected to the IR detector 28, the resonance amplifier being a narrow-band amplifier which is arranged to be regulable. A filter member and a rectifier are connected to the output of the resonance amplifier. A second detector 32 is located in front of the IR filter 22 and receives unfiltered radiation reflected from the front of the filter 22. The output voltage of the second detector 32 is amplified in an amplifier 34. A regulable reference voltage source 36 is connected to the amplifier 34. The resonance or signal amplifier 30 and the reference voltage source 36 are connected to a differential amplifier 50. A motor 38, which displaces the wedge 26 located in the path of the beam in front of the IR detector 28, is arranged to be direction-controlled by the differential amplifier 50 by way of a driver amplifier. The drive for the wedge 26 is connected to the slider of a precision potentiometer 40. The potentiometer 40 is located in the arm of an electrical bridge circuit 42. A digital indicator 44 is connected to the bridge diagonal by way of an analog-to-digital converter. A printer 46 is also connected to the digital indicator 44. The output voltage of the second detector 32 also has a frequency proportional to the rotational speed of the interrupting device 20. This output voltage of the second detector also acts as a control variable for a rotational speed stabilizer 48.

The rotational speed stabilizer compares the frequency fed thereto with a desired value and forms a control variable which is fed to the drive motor of the interrupting device.

Before the arrangement is put into operation, the wedge 26 is brought into a central position by regulating the amplification factor of the amplifier 30. The measuring chamber 14 is filled with pure air. The output voltage of the differential amplifier 50 is then zero. The indicator is then also set to zero by zero adjustment of the voltage of the bridge diagonal. Imbalance occurs at the input of the differential amplifier 50 upon blowing alcohol-containing breath into the measuring chamber 14, since the reference voltage remains the same, whereas the signal voltage does not remain the same. The differential amplifier 50 supplies an output voltage and the motor 38 starts. The motor pulls the wedge 26 out of the path of the beam until the attenuation reduced by the withdrawal of the wedge is equal to the absorption in the measuring chamber 14, and the signals in the two paths are again equal to one another, and the output voltage at the differential amplifier 50 thereby becomes zero again. The motor 38 stops. Displacement of the wedge by the motor is detected by the precision potentiometer 40 and indicated digitally on the indicator 44. By appropriate choice of the bridge voltage, this digital indicator 44 can be calibrated directly to shown blood alcohol concentration in parts per thousand. A peak value retainer 52 retains the maximum value. Alternatively, the result can be printed out by the printer 46. Similarly, the characteristic of the alcohol concentration with respect to time can be recorded by means of a recorder 54.

The second filter 24 is moved into the path of the beam and the measurement is repeated if the person being tested suffers from diabetes or if it is suspected that he is suffering from diabetes. By using the second measuring wave length, it can be established whether the measured breath actually contains alcohol and acetone. By limiting the measurement to the second filter 24, it is also possible, for the purpose of treating a diabetes patient, to obtain a reference value which the physician must know in order to administer the correct dose of insulin. The amplification in the amplifier 30 and the bridge voltage are changed over simultaneously with the changing of the filter in order to obtain equal readings with the two filters 22 or 24 in the case of alcohol absorption. This is effected by means of a microswitch which is actuated upon displacing the filter.

We claim:

1. An arrangement for determining the alcohol content of blood by measuring the concentration of alcohol in exhaled breath, comprising a measuring chamber, an inlet on the measuring chamber by which exhaled breath can be blown in, a radiation inlet at one end of the measuring chamber and a radiation outlet at the other end of the measuring chamber, a radiation source in the form of a wide band thermal radiator located upstream of the radiation inlet, an interrupting device in the path of the beam, a filter having a pass band at 3.46 $\mu$m arranged as a tuned receiver downstream of the radiation outlet of the measuring chamber, a first photoelectric detector arranged beyond the filter, a second detector arranged in the path of the beam beyond the radiation outlet of the measuring chamber and in front of the filter, an amplifier connected to the output of the first detector, reference voltage source connected to the output of the second detector, a differential amplifier connected to both the output of the amplifier and the output of the reference voltage source, a drive motor connected to the output of the differential amplifier, an absorption device which is displaceable in and at right angles to the path of the beam between the radiation outlet of the measuring chamber and the photo-electric detector, the absorption device being in the form of a wedge connected to the drive motor and having absorption in the band width of the filter, the drive motor being adapted to automatically displace the wedge to maintain at zero the voltage at the output of the differential amplifier and an indicator which is connected to the drive motor for the wedge and arranged to indicate the position of the wedge in the path of the beam.

2. An arrangement according to claim 1, having a second filter which is exchangeable for said first mentioned filter, the second filter having a pass band in the range of the absorption bands of acetone.

3. An arrangement according to claim 1, in which the second detector is arranged in the region of reflection of the filter and receives unfiltered radiation reflected from the front of the filter.

4. An arrangement according to claim 3, in which the interrupting device comprises a rotatable vane and a drive motor therefor and in which the output signal of the second detector additionally acts as a control variable for regulating the rotational speed of the interrupting device.

5. An arrangement according to claim 4, further comprising a device which is connected to the output of the second detector and which compares the frequency produced by the interrupting device with a reference value and feeds a regulating voltage, dependent upon this comparison, to the drive motor of the interrupting device.

* * * * *